US010806709B2

(12) United States Patent
Fleming

(10) Patent No.: US 10,806,709 B2
(45) Date of Patent: *Oct. 20, 2020

(54) INTRANASAL FORMULATION OF EPINEPHRINE FOR THE TREATMENT OF ANAPHYLAXIS

(71) Applicant: G2B Pharma Inc., Corte Madera, CA (US)

(72) Inventor: Nigel Ten Fleming, Tamariu (ES)

(73) Assignee: G2B Pharma, Inc., Corte Madera, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/698,208

(22) Filed: Sep. 7, 2017

(65) Prior Publication Data

US 2017/0368000 A1 Dec. 28, 2017

Related U.S. Application Data

(63) Continuation of application No. 13/929,100, filed on Jun. 27, 2013, now Pat. No. 9,789,071.

(60) Provisional application No. 61/664,790, filed on Jun. 27, 2012.

(51) Int. Cl.
| | | |
|---|---|---|
| A61K 31/137 | (2006.01) | |
| A61K 45/06 | (2006.01) | |
| A61K 31/277 | (2006.01) | |
| A61K 9/00 | (2006.01) | |
| A61K 31/417 | (2006.01) | |
| A61K 47/26 | (2006.01) | |
| A61K 47/38 | (2006.01) | |

(52) U.S. Cl.
CPC .......... *A61K 31/137* (2013.01); *A61K 9/0043* (2013.01); *A61K 31/277* (2013.01); *A61K 31/417* (2013.01); *A61K 45/06* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,407,481 | A | 10/1983 | Bolton et al. |
| 4,548,922 | A | 10/1985 | Carey et al. |
| 4,746,508 | A | 5/1988 | Carey et al. |
| 4,819,834 | A | 4/1989 | Theil |
| 5,023,252 | A | 6/1991 | Hseih |
| 5,731,303 | A | 3/1998 | Hseih |
| 6,284,765 | B1 | 9/2001 | Caffrey |
| 6,702,997 | B2 | 3/2004 | Chaudry et al. |
| 7,078,057 | B2 | 7/2006 | Kerkhof |
| 7,947,742 | B2 | 5/2011 | Batycky et al. |
| 7,954,491 | B2 | 6/2011 | Hrkach |
| 8,263,581 | B2 | 9/2012 | Du |
| 8,337,817 | B2 | 12/2012 | Nagata et al. |
| 9,789,071 | B2 | 10/2017 | Fleming |
| 2002/0161016 | A1 | 10/2002 | Tam et al. |
| 2003/0180283 | A1 | 9/2003 | Batycky et al. |
| 2003/0232078 | A1 | 12/2003 | Dong et al. |
| 2004/0219108 | A1 | 11/2004 | Dohi et al. |
| 2006/0233715 | A1 | 10/2006 | Oki et al. |
| 2008/0260848 | A1 | 10/2008 | Nagata et al. |
| 2010/0055152 | A1 | 3/2010 | Wahi |
| 2010/0178331 | A1 | 7/2010 | Nagata et al. |
| 2011/0033544 | A1 | 2/2011 | Nagata et al. |
| 2011/0237681 | A1 | 9/2011 | Batycky et al. |

FOREIGN PATENT DOCUMENTS

| | | |
|---|---|---|
| EP | 0096715 A1 | 12/1983 |
| EP | 0122036 A1 | 10/1984 |
| EP | 0193372 A2 | 9/1986 |
| EP | 2116264 A1 | 4/1987 |
| EP | 0444905 A1 | 9/1991 |
| EP | 1535615 A1 | 6/2005 |
| GB | 994734 A | 6/1965 |
| GB | 2 315 673 A * | 2/1998 |
| GB | 2315673 A | 2/1998 |
| WO | 199209034 A1 | 5/1992 |
| WO | 199211190 A2 | 7/1992 |
| WO | 2003037355 A1 | 5/2003 |
| WO | 2003/049791 A1 | 6/2003 |
| WO | 2007014391 A2 | 1/2007 |
| WO | 2010131486 A1 | 11/2010 |
| WO | 2011109340 A1 | 9/2011 |
| WO | 2011153400 A2 | 12/2011 |

OTHER PUBLICATIONS

Bleske et al. in American Journal of Emergency Medicine 13:133-138 (1996) (Year: 1996).*
Papich, M.G. in Saunders Handbook of Veterinary Drugs Small and Large Animal, Third Edition, Elsevier 2011 (Year: 2011).*
Bhise et al. in Asian Journal of Pharmaceutics 201-215 (2008) (Year: 2008).*
Reagen-Shaw et al. in FASEB Journal 22, 659-661 (2007) (Year: 2007).*
Extended European Search Report dated Apr. 3, 2017 in related matter EP Application No. 14842110.0, 16 pgs.
Papich, M.G. in Saunders Handbook of Veterinary Drugs Small and Large Animal, Third Edition, Elsevier 2011.
Fransen, N. in Studies of Novel Powder Formulation for Nasal Drug Delivery, Ph.D. Dissertation, Uppsala University, 2008.
Joint Task Force on Practice Parameters, 2005, J. Allergy Clin. Immunol., vol. 115, 2 pages.
Jung, S.Y., J. Allergy Clin. Immunol., vol. 125, No. 2, p. AB219.
Simons, F.E.R., First Aid treatment of anaphylaxis to food: Focus on epinephrine, J. Allergy Clin. Immunol., May 2004, pp. 837-843.
Constantino, et al., Intranasal delivery: Physiochemical and therapeutic aspects, International Journal of Pharmaceutics, 337 (2007), pp. 1-24.

(Continued)

*Primary Examiner* — Dennis Heyer
(74) *Attorney, Agent, or Firm* — Benesch, Friedlander, Coplan & Aronoff LLP

(57) ABSTRACT

This invention relates to pharmaceutical compositions of epinephrine for delivery to the nasal mucosa and methods of treating a subject in acute severe anaphylaxis, bronchospasm or during cardiopulmonary resuscitation (CPR). The composition further comprising agents, that either prevent localized degradation of epinephrine or enhance its absorption in the nasal mucosa to counter anaphylactic effects, symptoms or complications in a subject.

11 Claims, No Drawings

(56) References Cited

OTHER PUBLICATIONS

Tabor, D., Surface Forces and Surface Interactions, Journal of Colloid and Interface Science, vol. 58, No. 1, Jan. 1977, pp. 2-13.
Frew, A.J., What are the 'ideal' features of an adrenaline (epinephrine) auto-injector in the treatment of anaphylaxis, Allergy 2001: 16, pp. 15-24.
Rawas-Qalaji, et al., Epinephrine (adrenaline) absorption from new-generation, taste-masked sublingual tablets: A preclinical study, J. Allergy Clin. Immunol, Jan. 2013, pp. 236-238.
Takeuchi, et al., Novel mucoadhesion tests for polymers and polymer-coated particles to design optimal mucoadhesive drug delivery systems, Advanced Drug Delivery Reviews 57 (2005), pp. 1583-1594.
Good, R. J., Surface Fee Energy of Solids and Liquids: Thermodynamics, Molecular Forces, and Structure, Journal of Colloid and Interface Science, vol. 49, No. 3, May 1977, ISSN: 0021-9797, pp. 398-419.
Rawas-Qalaji, et al., Sublingual epinephrine tablets versus intramuscular injection of epinephrine: Does equivalence for potential treatment for anaphylaxis, J. Allergy Clin. Immunol., Feb. 2006, pp. 398-403.
Yamada, T., The Potential of the Nasal Mucosa Route for Emergency Drug Administration Via a High-Pressure Needleless Injection System, Anesth. Prog. 51 (2004) pp. 56-61.
Heilborn, et al. Comparison of subcutaneous injection and high-does inhalation of epinephrine—Implications of self-treatment to prevent anaphylaxis, J. Allergy Clin. Immunol., Dec. 1986, pp. 1174-1179.
Simons, et al., Epinephrine absorption in children with a history of anaphylaxis, J. Allergy Clin. Immunol., Jan. 1998, pp. 33-37.
Lieberman, p., Use of epinephrine in the treatment of anaphylaxis, Curr. Opin, Allergy Clin. Immunol., (2003) pp. 313-318.
Simons, et al., Can Epinephrine Inhalations be Substituted for epinephrine Injections in Children at Risk for Systemic Anaphlaxis, Pediatrics Official Journal of the American Academy of Pediatrics (200), pp. 1040-1044.
Lieberman, et al., The diagnosis and management of anaphylaxis: An updated practice parameter, J. Allergy Clin. Immunol., Mar. 2005, pp. S483-S523.
Notification of Transmittal of the ISR and the Written Opinion of the ISA, dated Dec. 22, 2014, for PCT/US2014/053700, Int'l Filing Date of Sep. 2, 2014.
McNally, B., et al., Out-of-Hospital Cardia Arrest Surveillance—Cardiac Arrest Registry to Enhance Survival (CARES), 2011, MMWR Surveill Summ. 60(8): 1-19.
Roger, V. L., et al., Heart Disease and Stroke Statistics—2011 Update: A Report from the American Heart Association, 2011, Circulation 123: e18-e209, pp. 1-388.
Jacobs, I., et al., Cardiac Arrest and Cardiopulmonary Resuscitation Outcome Reports, 2004, Circulation 110(21): 3385-97.
Wik, L., et al., Quality of Cardiopulmonary Resuscitation During Out-of-Hospital Cardiac Arrest, 2005, JAMA 293: 299-304.
Callaway, C. W., et al., Receiving hospital characteristics associated with survival after out-of-hospital cardiac arrest 2010, Resuscitation 81: 524-529.
Yakaitis, R.W., et al., Relative importance of $\alpha$ and $\beta$ adrenergic receptors during resuscitation, 1979, Crit. Care Med. 7: 293-96.
Otto, C.W., et al., The Role of Epinephrine in CPR: A reappraisal, 1984, Ann. Emerg. Med. 9 pt. 2: 840-843.
Field, J.M., et al., 2010 American Hear Association Guidelines for Cardiopulmonary Resuscitation and Emergency Cardiovascular Care, 2010, Circulation122 (18 Supple 3): S640-56.
Paradis, N.A., et al., The effect of Standard-and High-Dose Epinephrine on Coronary Perfusion Pressure During Prolonged Cardiopulmonary Resuscitation, 1991, JAMA 265(9): 1939-44.
Niemann, J.T. et al., Endotracheal drug administration during out-of-hospital resuscitation: where are the survivors? 2002, Resuscitation 53(2): 153-7.
Callaway, C.W., Epinephrine for cardiac arrest, 2013, Curr. Opin. Cardio. 28(1): 36-42.
Lapostolle, F. et al., Endpoints in studies on myocardial infarction, 2007, Lancet 369(6571): 1430.
Hagihara A., et al. Prehospital Epinephrine Use and Survival Among Patients with Out-of-Hospital Cardiac Arrest, 2012, JAMA 307(11): 1161-1168.
Nakahara S., et al., Continuing Medical Education Activity in Academic Emergency Medicine, 2012, Acad. Emerg. Med. 19(7): 782-92.
Hess, E.P. and White, R.D. Optimizing Survival from Out-of-Hospital Cardiac Arrest, 2010, J. Cardiovsc. Electrophsiol. 21(5): 590-95.
Bleske, B.E., et al., Comparison of Intravenous and Intranasal Administration of Epinephrine During CPR in a Canine Model, 1992, Ann. Emerg. Med. 21(9): 1125-1130.
Bleske, B.E.,et al., Effect of Dose on the Nasal Absorption of Epinephrine During Cardiopulmonary Resuscitation, 1996, Am. J. Emerg. Med. 14: 133-138.
Bleske, B. E., et al. Effect of Vehicle on the Nasal Absorption of the Epinephrine During Cardiopulmonary Resuscitation, 1996, Pharmacotherapy 16(6): 1039-1045.
Nakponetong, K., et al., Pharmacokinetics of Epinephrine Absorption via Intranasal Administration: A Preliminary Report, 2010, J. Allergy Clin. Immunol. 125(2): Abstract 859.
Tabor, et al., Surface Forces and Surface Interactions, 1977, J. Colloid Interface Sci. 58:2.
Gu, X., et al. Epinephine Absorption after Different Routes of Administration in an Animal Model, 1999, Biopharm Drug Dispos., 20: 401-405.
Abella, B.S., Quality of Cardiopulmonary Resuscitation During In-Hospital Cardiac Arrest, 2005, JAMA 293:3, pp. 305-310.
Haruta S. "A Nasal Delivery Solution to the Challenges in Biotherapeutic Delivery", (ONdrugDelivery, 2012, Issue No. 38, pp. 14-17).

\* cited by examiner

INTRANASAL FORMULATION OF EPINEPHRINE FOR THE TREATMENT OF ANAPHYLAXIS

REFERENCE TO RELATED APPLICATION(S)

This application is a continuation of U.S. patent application Ser. No. 13/929,100 filed on Jul. 27, 2013, which claims the benefit of U.S. Provisional Application No. 61/664,790, filed Jun. 27, 2012. The entire teaching of the above application is incorporated herein by reference.

FIELD OF THE INVENTION

The invention relates to pharmaceutical compositions of epinephrine suitable for intranasal administration and methods of using the composition to treat anaphylaxis, bronchospasm, and during cardiopulmonary resuscitation (CPR).

BACKGROUND OF THE INVENTION

Anaphylaxis is a severe, rapid onset allergic reaction to insect stings or bites, foods, drugs, allergens, and can be idiopathic or exercise-induced. About 3 million American children suffer from food allergies (from peanuts, tree nuts, milk, eggs, fish, seafood and gluten) and according to a study released in 2008 by Centers for Disease Control and Prevention, there has been about an 18% increase in food allergy since 1997. Anaphylaxis occurs in about 1-16% of the US population and carries a 1% mortality rate. Epinephrine (adrenaline) is the uncontested cornerstone for the treatment of anaphylaxis, and can be lifesaving (Joint Task Force on Practice Parameters, 2005, J Allergy Clin Immunol 115: S483-S523; Lieberman P. 2003, Curr Opin Allergy Clin Immunol 3: 313-318; Simons F.E.R. 2004, J Allergy Clin Immunol 113: 837-844). Any delay in administration of epinephrine may be fatal. In 2003, 1.4 million intramuscular (IM) doses (EpiPen™) were prescribed in the United States and it increased to 1.9 million by 2007. About 100-200 people die annually in the US from food allergies.

Epinephrine, being the first-line of therapy for anaphylaxis, is available only as an injectable dosage form in ampoules or in autoinjectors (e.g., EpiPen™ and Adrenaclick™ Autoinjector). It is well absorbed systemically when administered by intramuscular (IM) or subcutaneous (SQ) routes. Subcutaneous injection has been shown to result in delayed (slower Tmax) and variable adrenaline absorption and hence not very effective (Simons F.E.R. et al. 1998, J Allergy Clin Immunol 101:33-37). IM injection, on the other hand, is favored over SQ route because of its rapid onset of action (Tmax) of about 3-8 minutes, and the duration of action between 1 and 4 hours. Based on historical and anecdotal evidence, a 0.3 mg dose of epinephrine, by subcutaneous (SQ) or intramuscular (IM) injection into the deltoid muscle, has been agreed upon as the dose required for the emergency treatment of adult anaphylaxis. Recent studies have also demonstrated that if 0.3 mg dose is administered IM into the laterus vascularis (thigh) muscle, epinephrine plasma concentrations are higher and occur more quickly than SQ or IM administration into the deltoid muscle (Joint Task Force on Practice Parameters, 2005, J Allergy Clin Immunol 115: S483-S523; Lieberman P. 2003, Curr Opin Allergy Clin Immunol 3: 313-318; Simons F.E.R. 2004, J Allergy Clin Immunol 113: 837-844)).

Thus, epinephrine injections are administered either manually or by automatic injectors preferably by IM route. However, there are many difficulties associated with manual SQ or IM administration of epinephrine, as discussed by Frew A. J. 2011, Allergy 66:15-24, that include: (i) well-known patient apprehension related to needle delivery, (ii) incorrect self-administration, (iii) extra-operational step of detaching the needle shield before removal of safety cap in syringe based injectors, (iv) possible loss of medication before reaching the target muscle, (v) requiring a trained or medical professional to administer the dose, and (vi) needle-stick injury. In addition, patients also find that the device is awkward to carry, especially as a second device is indicated in case of rebound anaphylaxis (20% of cases). Patients are therefore recommended to have at least one autoinjector at home, in the car, and at school or work, but few have them in all locations. As a result of these difficulties, the majority of at-risk diagnosed patients either does not fill their prescription for an autoinjector, or are unwilling to use it, instead going to the Emergency Department.

In addition, the currently marketed Epipen™ comes in two fixed doses of 0.15 mg for pediatric patients and 0.3 mg for adults, which often forces physicians to decide whether to under- or overdose a patient based on weight, especially in children. Hence, there exists a need in the market for more convenient, easy delivery of correct dosage form that does not require prior training in the use of the device, and increase compliance in persons prone to anaphylaxis. The intranasal formulations of present invention can be delivered using a small needle-free nasal spray device, which is simple to operate, easy to (self) administer and require no prior training to deliver therapeutic dose(s) thus enhancing compliance in individuals. Because the device is small, it is also easy to carry them unobtrusively in the pocket. Importantly, by providing 2 nasal sprays of the present formulation; a higher dose for adults, a lower dose for pediatric patients and an option to deliver the required dose (based on body weight by repeating the sprays) or a second dose in situations of rebound anaphylaxis, the present invention solves some of the important practical limitations of the autoinjector.

Delivery of epinephrine by oral route is also not recommended because of negligible bioavailability owing to its rapid and extensive metabolism in the gut and liver. Hence as an alternative approach, Rawas-Qalaji M. M. et al. (2013, J Allergy Clin Immunol. 131(1): 236-38; 2006, J Allergy Clin Immunol. 117(2): 398-403 and in WO2011109340) attempted to deliver epinephrine via the sublingual (SL) route. The authors used a very large loading dose of SL epinephrine (40 mg) probably due to its mucosal enzymatic degradation by COMT, as well as poor intrinsic mucosal transportation due to the strong vasoconstriction caused by epinephrine itself. The study further revealed that SL doses ranging from 5 to 40 mg epinephrine, as the bitartrate salt, could achieve plasma concentrations equivalent to IM injection. Despite the promise of this needle-free delivery approach, the disadvantage of vomiting associated with anaphylaxis and the panic in anaphylacting patients is a serious constraint to its practical use, making it highly unlikely that the SL tablet will stay in place under the tongue for sufficient time to be therapeutically effective. The intranasal spray formulations of the present invention, on the other hand, allows for a pharmaceutical dose to be delivered easily by the caretaker or patient as required and without major difficulties or undesired effects.

Early methods of nasal drug delivery employed relatively harsh methods to transport drugs across the nasal mucosa, including the use of damaging permeation enhancers such as bile salts. Consequently, many of the nasally delivered drugs were traditionally limited to nasal conditions such as rhinitis and nasal allergies, where the drugs act topically on the nasal mucosa rather than enter the systemic circulation. More recently, however, systemically acting nasally administered drugs, have been successfully developed.

The potential for delivering aqueous epinephrine solution via nasal mucosa route using a needleless high-pressure injection device was attempted by Yamada T. 2004, Anesth Prog 51: 56-61 in dogs. Using this delivery approach, the author reported achieving a peak (Tmax) epinephrine levels of ~20 ng/mL in the blood at 15 seconds. The peak systolic pressure was 200% of baseline at 60 seconds and maintained for about 180 seconds, confirming physiological effects of epinephrine. Yet, this type of delivery is painful resulting in poor compliance and limited routine clinical utility. On the contrary, the intranasal formulation of the present invention is painless as it is delivered as a nasal spray, further contributing to enhanced patient compliance.

Pulmonary delivery of systemic epinephrine has been explored by Heilborn H. et al. 1986, J Allergy Clin Immunol. 78(6): 1174-79. The study compared the effects of high-dose pulmonary inhalation of epinephrine (i.e., 1.5 to 4.5 mg and 10 to 30 inhalations over several minutes from a metered-dose aerosol) versus subcutaneous injection in human subjects. The results showed that inhalation of 2 to 3 mg of epinephrine produces a gradual increase of epinephrine concentrations in plasma and hence may be beneficial to counteract the effects of bronchoconstriction in night-time asthma. Bronchomist™ was approved for this indication as an inhaled epinephrine mist. However, similar studies by Simons F. E. R. et al. 2000, Pediatrics 106(5): 1040-44 tested whether this could be used for anaphylaxis patients, and concluded that the number of inhalations required especially for children, the length of time to reach a threshold Tmax, and the unpleasant taste, made the pulmonary inhalation delivery route unacceptable for treating anaphylaxis. By providing an intranasal formulation that contains taste-masking agents and an optimal dose of epinephrine required to reach a Tmax equivalent to IM administered epinephrine, the present invention has overcome the limitations noted by the above-mentioned art.

The important intranasal epinephrine studies were conducted by Bleske B. E. et al. 1996 Am J Emerg Med 14: 133-38, who showed the systemic administration of epinephrine by the nasal route, for treatment of dogs during cardiopulmonary resuscitation (CPR). Although these authors observed a dose response, the absolute bioavailability appeared to be quite low, despite the use of 1% taurodeoxycholic acid solution (bile salts), which is now known to be a damaging mucosal permeation enhancer. Moreover, to minimize the severe local vasoconstriction caused by epinephrine that could potentially limit the mucosal absorption of epinephrine, they used pretreatment with intranasal phentolamine. The phentolamine pretreatment was administered 1 min prior to intranasal epinephrine dosing to enhance epinephrine absorption. To prevent its local degradation on the external nasal mucosa, the investigators used large loading doses of phentolamine ranging from 0.25 to 2.5 mg/kg/nostril, which amounts to 15 mg for a dog weighing 21 kg. The loading doses of epinephrine studied were 0.075, 0.75 and 7.5 mg/kg/nostril, which amounts to 157 mg/nostril for a dog weighing 21 kg. The greatest cardiac effects and the greatest epinephrine plasma concentrations of about ~1,400 ng/mL were observed at 0.25 mg/kg/nostril of phentolamine and 7.5 mg/kg/nostril of epinephrine. For optimal treatment the authors used 7.5 mg/kg/nostril of epinephrine with 1% taurodeoxycholic acid as permeation enhancer after pretreatment with 0.75 mg/kg/nostril in about 1 ml each application. Although this study revealed the systemic delivery of epinephrine by the nasal route of administration, it had significant limitations for translation into clinical practice, including: (i) dosing that was not optimized, and it is also unclear whether phentolamine was used at its lowest level with no or minimal systemic exposure (which would have competed with epinephrine actions); (ii) the staged pre-dosing of phentolamine followed by epinephrine, which is totally impractical for real-world emergency treatment; (iii) the use of a very large loading dose of epinephrine (157 mg/nostril for a dog weighing 21 kg) and vasodilator (15 mg/ nostril for a dog weighing 21 kg); (iv) use of large volumes such as 1.0 mL of solution per nostril and even at that volume, the epinephrine was noticed to crystallize out; this large volume in each nostril is also impractical for modern nasal aqueous sprays which use only 100-250 µl volume, and even at this lower volume quite a significant percentage of the aqueous dose slides off the more dense nasal mucosa and is swallowed; (v) the use of bile salts as mucosal permeation enhancers caused severe nasal mucosal tissue damage, and raises the question to what extent was the systemic delivery achieved due to the destruction of this tissue barrier, rather than by the actual penetration by epinephrine. This safety aspect of the study was a fatal flaw for clinical translation of this technology. This technology has lain dormant with no follow-up studies of any kind since 1996.

A nasal spray with a high loading dose of epinephrine (5 mg) was given to normal human subjects and was compared with intramuscular epinephrine in a recent study by Nakponetong K. et al. 2010, J Allergy Clin Immunol 125(2): Abstract 859. The study revealed a peak plasma concentration (Tmax) reached in 70±17 minutes. A Tmax of 70±17 minutes even at the higher loading dose of epinephrine, is insufficient to be of any utility in anaphylactic shock. Paradoxically, the data on the PK of the IM epinephrine injection with a Tmax of 69±19 minutes is also unacceptable.

Epinephrine formulations delivered by dry powder inhaler, which targets nasal mucosa of a subject and administered by breath-activated devices are described in two U.S. Pat. Nos. 7,954,491 and 7,947,742. However, such delivery of epinephrine may not be practically feasible in persons already in anaphylactic shock. Patient-activated devices are simply not suitable for treating children in an emergency anaphylactic setting. No successful systemic delivery or formulations were described.

Hence, despite the theoretical promise for the intranasal route for delivering epinephrine, there is a need for novel approaches for improving the intranasal (IN) epinephrine formulation for the treatment of anaphylaxis. As noted above, the investigation by Bleske B. E. et al. 1996 also had a number of significant practical limitations that prevented their clinical translation. And the lack of any successful follow-on studies has left this advance of 1996 frozen in time.

The present invention, however, has solved all the critical limitations of the above-mentioned art, especially the Bleske study. The first innovation is formulation. The formulation of the present invention permits lowering the epinephrine loading dose by the optional addition of a reversible topically-acting COMT inhibitor (to prevent epinephrine enzymatic degradation at the nasal mucosa), which may be co-administered with a low dose of a topically-acting vasodilator (phentolamine, to stop inhibition of mucosal transport by gross vasodilation) with epinephrine at the same time in the same dose. Added to these are one or more or combination of mucosal transit slowing agents, and modern permeation enhancers that are non-toxic to nasal tissues. The second innovation is to deliver this as a powder formulation, which itself is muco-adhesive and aids in mucosal dissolution and absorption. The resulting nasal route of administration to achieve systemic epinephrine in therapeutic doses sufficient to treat anaphylaxis, bronchospasm and coronary arrest is: (i) painless (no needle-phobia); (ii) easy to (self) administer or to have a caregiver administer; (iii) uses practical small doses of intranasal epinephrine formulation containing epinephrine, a vasodilator, COMT inhibitor, mucosal transit slowing agents, and modern permeation enhancers that are not toxic to nasal tissues.

The present invention represents the first major step forward in nasal epinephrine delivery since Bleske in 1996 and is neither anticipated nor is obvious to those with ordinary skills in the art.

SUMMARY OF THE INVENTION

Accordingly, the present invention is directed towards a pharmaceutical composition comprising: (i) an anti-anaphylactic agent; (ii) a reversible COMT inhibitor to arrest mucosal enzymatic degradation of epinephrine, which permits use of lower epinephrine loading dose and optimal solubility limits that does not require unmanageably large liquid volumes (in case of an aqueous spray) or the physical weight (in case of a dry powder administration); and/or (iii) a vasodilator suitable for intranasal administration to elicit a systemic therapeutic response during anaphylaxis.

According to the first aspect of invention, the anti-anaphylactic agent in the composition is epinephrine, present in amounts ranging from 0.05 mg to 10 mg, preferably from 0.05 mg to 0.75 mg or 0.75 mg to 1.5 mg or 1.5 mg to 3.0 mg or 3.0 to 4.5 mg or 4.5 to 6.0 mg or 6.0 to 7.5 mg or 7.5 to 9.0 mg or 9.0 to 10.0 mg. In a related aspect, a single dose of epinephrine given intranasally is bioequivalent to IM or SQ injected epinephrine (using Epipen™ autoinjector of 0.15 mg for pediatric and 0.3 mg for adult patients). In another aspect, the epinephrine dose may be adjusted according to the weight of the patient at an increment of at least 0.01 mg/kg, or one wherein the dose may be repeated a number of times if the patient is refractory or experiences rebound anaphylaxis. The present intranasal epinephrine composition provides an initial rise in epinephrine plasma levels which is at least 2-fold, preferably 3 to 10-fold more than baseline levels, within 20, 15, 10, 5 and 3 minutes (Tmax), followed by a sustained therapeutic efficacy of the drug for at least 60, 50, 40, 30 minutes after administration.

In addition to epinephrine, the intranasal pharmaceutical composition of the present invention comprises a reversible COMT inhibitor and/or a vasodilator. In a preferred embodiment, the reversible COMT inhibitor in the intranasal composition of the present invention is entacapone, present in the amounts between 0.001 mg (or 1 μg) and 10 mg, preferably from 0.001 mg to 0.01 mg or 0.01 mg to 0.05 mg, 0.05 to 0.1 mg, 0.1 to 0.5 mg, 0.5 to 0.75 mg, 0.75 mg to 1.5 mg or 1.5 mg to 3.0 mg or 3.0 to 4.5 mg or 4.5 to 6.0 mg or 6.0 to 7.5 mg or 7.5 to 9.0 mg or 9.0 to 10.0 mg. In a yet another preferred embodiment, the vasodilator in the intranasal composition is phentolamine, present in the amounts between 0.001 mg and 10 mg, preferably from 0.001 mg to 0.01 mg or 0.01 mg to 0.05 mg, 0.05 to 0.1 mg, 0.1 to 0.5 mg, 0.5 to 0.75 mg, 0.75 mg to 1.5 mg or 1.5 mg to 3.0 mg or 3.0 to 4.5 mg or 4.5 to 6.0 mg or 6.0 to 7.5 mg or 7.5 to 9.0 mg or 9.0 to 10.0 mg. These sub-clinical doses of the enabling agents are designed so as to prevent appreciable entry into systemic circulation, and thus to act only topically on the nasal mucosa. In another related aspect, the intranasal epinephrine composition of the present invention may further comprise one or more or combination of additional agents selected from the group of epinephrine potentiator, a mucosal permeation enhancer, an agent that reduces mucosal transit time, an agent that increases mucosal absorption or adhesion or transport, surfactants, chelators, pharmaceutically acceptable excipients, non-sulfite stabilizers, preservatives, thickening agents, humectants, antihistamines, solubilizing agents, taste and smell masking agents, antioxidant enzymes, viscosity enhancing agents, dispersing agents, colorants, or any combination thereof.

In a second aspect of the invention, the intranasal composition in accordance with the present invention can be aqueous or dry powder composition. In a preferred aspect, the composition is administered in the form of dry powder due to its many advantages over aqueous nasal formulations, which include but are not limited to: (i) API stability, especially in a mixture which can be challenging to find a common aqueous buffer that permits maximal stability of unstable APIs; (ii) the powder easily incorporates into the nasal mucous layer and increases the absolute nasal residency time of the API, while an aqueous nasal spray will more likely encounter the mucous layer and due to the density differences, simply slide off into the throat, and not deliver the API to the nasal mucosa; (iii) dry powder formulations permit the API to immediately embed into the mucosal layer and then dissolve, causing an effective concentration gradient for the drug across the mucosal membrane; (iv) as a dry powder, it permits further incorporation of a nasal mucosal permeation enhancer, a epinephrine potentiator, an agent that reduces mucosal transit time, an agent that increases mucosal absorption or adhesion, and or an agent that enhances mucosal transport. Powder nasal administration is a very recent development in nasal drug delivery and was not anticipated in the time of Bleske's studies. Furthermore, there are a large number of modern and safe nasal permeation enhancers available that can replace the toxic bile acids used in the original studies.

Accordingly, the dry powder composition is prepared in amounts of up to 100 mg, preferably from 10 to 20 mg or 20 to 40 mg or 40 to 60 mg or 60 to 80 mg with median particle diameter of up to 30 μm and containing any pharmaceutically acceptable carrier, such as lactose or any one or more or combination of enabling agents that promote adhesion or absorption to nasal mucosa such as mucoadhesives or mucosal transit slowing agents or mucosal absorption and permeation or penetration or transport enhancers. The active ingredients of powdered composition can be substantially amorphous or crystalline. In some preferred embodiments, the shape of the particles is diverse.

In yet another embodiment, the active ingredients (epinephrine, reversible COMT inhibitor and/or vasodilator and one or more enabling agents) are nanoformulated or not nanoformulated. Nanoformulation for a liquid formulation that is reconstituted shortly prior to use is designed to overcome the solubility limits to ensure that the resulting aqueous volume is kept to the minimum, optimally 100-250 μl. When the composition is present in the form of nanoparticles it could be reconstituted in a pharmaceutically acceptable liquid prior to use, optionally where the liquid contains one or more pharmaceutically acceptable excipients. If the composition is dissolved in aqueous milieu, it contains one or more pharmaceutically acceptable excipients such as: epinephrine potentiator, a mucosal permeation enhancer, an agent that reduces mucosal transit time, an agent that increases mucosal absorption or adhesion, an agent that enhances mucosal transport, a buffer, tonicifier, stabilizer, viscosity enhancing agent, preservatives, colorants or any combination thereof to adjust pH and osmolarity.

In a third aspect, the present invention provides a pharmaceutical product, comprising apparatus for intranasally administering a pharmaceutical dose or dose form in accordance with the pharmaceutical composition of the invention. The apparatus can comprise a reservoir and means for expelling the pharmaceutical dose in the form of a spray, wherein a quantity of the pharmaceutical composition is contained within the reservoir. In an embodiment, the apparatus comprises a pump spray device in which the means for expelling a single or multiple doses comprises a metering pump, or a sterile single dose disposable device. The dose to be delivered is typically metered by the spray pump, which is preferably finger or hand-actuated. In some embodiments, the device is programmed to dispense one or more pharmaceutical dose. The nasal spray is designed for discharge of multiple spray doses, e.g., 1 to 10 or more. It may be designed to administer the intended dose with multiple sprays, e.g., two sprays, e.g., one in each nostril, or as a single spray, e.g., in one nostril, or to vary the dose in accordance with the body weight or maturity of the patient. The object of the design of the safety spray device is to assure to the extent possible that a consistent loading dose of epinephrine, which is the blood equivalent of IM or SQ administered epinephrine dose (0.15 mg in pediatric and 0.3 mg in adults) is delivered to the bloodstream to counteract the anaphylactic effects in a subject.

In a further aspect, the composition may also be administered using a nasal metered dose spray, metered dose inhaler or measured dose inhaler. In another aspect, when the composition is aqueous, volumes of up to 200 μcan be delivered using a pharmaceutical aerosol device.

In a yet further aspect, the present invention is also directed towards a composition for single or multiple use dosage unit form, including a sterile disposable dosage form that contains no preservatives.

In a fourth aspect pharmaceutical compositions, doses or products in accordance with the present invention are useful in the treatment of anaphylaxis, bronchospasm or cardiac arrest in subjects or for increasing mean arterial pressure in subjects outside ER or situations in battlefield or hypotensive shock. They also provide a fast onset time and are suitable for intranasal use. Although not wishing to be bound by any particular theory, it is considered that the capacity of compositions in accordance with the present invention for providing high blood plasma epinephrine concentrations rapidly after administration.

Accordingly, the present invention is also directed toward methods for treating anaphylaxis in an individual, comprising, applying to the mucosal surfaces of the nasal cavities of an individual (the mucosal surfaces of the anterior regions of the nose, the frontal sinus and the maxillary sinuses and on each of the mucosal surfaces which overlie the turbinates covering the conchas) any of the above described pharmaceutical compositions by administering a nasal epinephrine loading dose (i.e., the amount of epinephrine administered nasally which results in the systemic blood bioequivalent of intramuscularly administered EpiPen™, for the 0.15 mg and 0.3 mg doses of EpiPen™) In a related aspect, the method of treating a patient with anaphylaxis or bronchospasm in need of treatment from a nasal loading dose of about 0.05 mg to about 10 mg of epinephrine, about 0.001 mg (or 1 μg) to about 10 mg of a vasodilator, about 0.001 mg (or 1 μg) to about 10 mg of a reversible COMT inhibitor, and about 0.001 mg (or 1 μg) to about 10 mg of a epinephrine potentiator a mucosal permeation enhancer, an agent that reduces mucosal transit time, an agent that increases mucosal absorption or adhesion, an agent that enhances mucosal transport, (or the enantiomers, diastereoisomers, racemates, prodrugs thereof, and the salts of such compounds with pharmaceutically acceptable counterions), wherein said amounts are synergistic for the treatment of anaphylaxis, bronchospasm or cardiac arrest.

DETAILED DESCRIPTION OF INVENTION

Unless defined otherwise, all technical and scientific terms used herein have the same meaning as commonly understood by one of the ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods and examples are illustrative only and not limiting.

The singular forms "a," "and" and "the" are used herein to include plural references unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

The term anaphylaxis refers to an acute, systemic allergic reaction that occurs after an individual has become sensitized to an antigen. It is associated with the production of high levels of IgE antibodies and with the release of histamines, which cause muscle contractions, constriction of the airways (bronchospasm), and vasodilation. Symptoms of anaphylactic reactions include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, intercostals retractions, etc. Possible complications of severe anaphylactic reaction include airway blockage, cardiac arrest, respiratory arrest, shock, and sometimes death. The intranasal formulations of the present invention can treat anaphylactic shock and/or symptoms and complications arising due to anaphylaxis. In another embodiment, the present intranasal formulation can be used to increase mean arterial pressure in a subject during CPR or in battlefield situations and hypotensive shock.

"Enabling agents" according to the present invention refers to compounds or agents that act synergistically with epinephrine to enhance or promote its action or absorption or adhesion in target tissue to cause amelioration of the anaphylactic symptoms in a subject. Accordingly, the enabling agents include one or more of the following in any combination; a reversible COMT inhibitor, vasodilators, epinephrine potentiators, permeation or penetration enhancers or mucosal absorption or transport enhancers, agents that reduce mucosal transit time, thickeners, anti-histamines and others as described henceforth.

As described earlier, intranasal epinephrine formulations disclosed in prior-art either have no enabling agents in their formulation (Nakponetong K. et al. 2010, J Allergy Clin Immunol 125(2): Abstract 859) or use impractical amounts and doses of epinephrine and vasodilator in their composition (Bleske B.E. et al. 1996 Am J Emerg Med 14: 133-38) to rescue animals from cardiac arrest. It is therefore the primary object of the invention to utilize a novel composition of epinephrine that contain effective doses and volumes of enabling agents that is suitable for intranasal administration to ameliorate specifically the effects of anaphylaxis, bronchospasm, or cardiac arrest, in a subject.

Accordingly, to achieve the primary objective of the present invention, the composition comprises the following:

(i) The anti-anaphylactic agent in the present invention is epinephrine, such as epinephrine hydrochloride, epinephrine free base, epinephrine maleate, epinephrine bitartrate, epinephrine methyl ester or hydrochloride, glycosyl epinephrine derivatives, dipavalyl epinephrine derivatives including dipivefrin hydrochloride, dipivalyloxy catecholamine derivatives, and dipivalyl prodrugs, or the enantiomers, diastereoisomers, racemates, prodrugs, and the salts of such compounds with pharmaceutically acceptable counterions, or any combinations thereof. In a preferred embodiment, the anti-anaphylactic agent is epinephrine, or its pharmaceutically acceptable salts thereof. In other embodiments, the anti-anaphylactic agent is epinephrine hydrochloride. In certain other embodiments, the anti-anaphylactic agent is epinephrine maleate.

In a yet other preferred embodiment, the anti-anaphylactic agent epinephrine is combined with subclinical levels of a reversible Catechol-O-Methyl Transferase (COMT) inhibitor, which reduces the action of natural COMT enzymes that degrade epinephrine on the nasal mucosa. Consequently, this allows use of lower epinephrine doses for administration in the present invention, further reducing local tissue irritation, and other adverse side effects, that are dose-dependent. Reducing the loading dose of epinephrine also reduces the amount of API needed, making the solubility limit of aqueous delivery or the mg weight burden of powder delivery, more practical. Inhibiting the action of naturally present COMT enzymes is an approach used in the treatment of Parkinson's disease. These patients degrade the powerful Parkinson's drug, L-Dopa via COMT and as a counter measure, the FDA approved use of inhibitors of oral COMT for Parkinson's treatment. In the present invention, drug in this class are used in a novel way, to reduce the degradation of epinephrine by COMT and potentiate or enhance the potency of epinephrine.

(ii) Accordingly, the FDA approved reversible COMT inhibitor included at subclinical concentrations, designed to have the minimal systemic exposure and to be acting mainly topically, is selected from the group comprising of the nitrocatechols, entacapone or tolcapone, Comtan (entacapone), Stalevo (entacapone plus carbidopa and levadopa) and Tasmar (or the enantiomers, diastereoisomers, racemates, prodrugs, and the salts of such compounds with pharmaceutically acceptable acids and bases). In a preferred embodiment, the reversible COMT inhibitor in the intranasal epinephrine composition is entacapone. In other embodiment, the reversible COMT inhibitor in the intranasal epinephrine composition is tolcapone.

(iii) The current invention also provides for intranasal formulations of epinephrine that avoids local tissue vasodilation, observed in epinephrine injections. As noted earlier, FDA-approved vasodilator is added at subclinical concentrations to reduce the nasal vascular vasoconstriction caused by epinephrine and allows faster flux across the mucosal membrane, designed to have the minimal systemic exposure and to be acting mainly topically. This further enables use of lower loading doses of epinephrine, thereby reducing dose-related adverse side effects.

Accordingly, the vasodilators added to the present formulation of the invention are selected from but are not limited to older vasodilators, (i.e., hydralazine, isosorbide mononitrate, isosorbide dinitrate) ACE inhibitors (i.e., Benazepril (Lotensin), Captopril (Capoten), Enalopril (Vasotec), Fosinopril (Monopril), Lisinopril (Prinivil, Zestril), Minoxidil (Loniten), Meoexipril (Univasc), Perindopril (Aceon), Quinapril (Accupril), Ramipril (Altace), Trandolaptril (Mavik)), and Angiotensin II receptor agonists (A2 inhibitors) (i.e., Losartan, Candesatran, Valsartan, Irbesartan, Telmisartan, Eprosartan, Olmesartan, Azilsartan), and others including papaverine hydrochloride or phentolamine mesylate, selected from: cocaine; ethyl nitrate; nitroglycerine; diltiazem; urapidil; nicorandil; sodium nitroprusside; glyceryl trinitrate-verapamil; phenoxybenzamine; dopexamine; chloropromazine; propiverine hydrochloride; (or the enantiomers, diastereoisomers, racemates, prodrugs, and the salts of such compounds with pharmaceutically acceptable acids and bases. In a preferred embodiment, the vasodilator present in the intranasal composition is phentolamine.

The present invention also contemplates adding to the formulation one or more or combination of the following enabling agents:

(a) Epinephrine potentiators that improve or enhance the pharmacological action of epinephrine. Such potentiators are selected from the group comprising of guanethidine, selected from NAC; isoproterenol; norepinephrine; hydrocortisone; flavonoids (vitamin-P like compounds; local anesthetics; vasopressin; cocaine; methylphenidate; tripelennamine; bufozenine; harmine; mescaline; LSD; methergine; ganglionic blockers; antihistamines; amphetamines, or the enantiomers, diastereoisomers, racemates, prodrugs, and the salts of such compounds with pharmaceutically acceptable counterions, or any combination thereof. Other agents that potentiate epinephrine responses by inhibiting its degradation by COMT include tropolone, desmethyl papaverine and pyrogallol. Certain amino acids, including histidine in the presence of tissue cupric ions, also potentiate epinephrine action.

Further, compounds such as flavinoids (Vitamin P-like compounds), local anesthetic agents, vasopressin, cocaine, methylphenidate (Concerta the CNS stimulant for ADHD), tripelennamine, bufotenine, harmine, mescaline, LSD, methergine, ganglionic blockers, antihistamines (norepinephrine), and amphetamines may also be used to potentiate epinephrine.

(b) Permeation enhancer as used herein, refers to one or mixture of substances which when formulated with anti-anaphylactic agent, such as epinephrine have the effect of increasing the fraction of the epinephrine applied to the nasal mucosal surface that traverses the mucosal membrane and enters bloodstream, i.e., increases bioavailability. Generally, the addition of a permeation enhancer to epinephrine formulation designed for intranasal administration will increase the fraction of epinephrine that reaches the circulation by at least about 25%, preferably at least 50%, and most preferably at least 100%. Many such permeation enhancers are known, as described herein. The present invention contemplates adding nasal permeation or nasal penetration enhancers such as bile salts, alkyl glycoside, polymer, tight junction modulating peptides as described in WO2007014391 A2, lipids, surfactants, cyclodextrin, or chelators, or any combination thereof. Cyclodextrins can have various functions in the intranasal formulation, including taste masking, drug solubilization, and drug stabilization. Cyclodextrins have also been found to have unexpected synergistic effects when combined with certain permeation enhancers. Examples of pharmaceutically acceptable cyclodextrins include alpha-cyclodextrin, beta-cyclodextrin, gamma-cyclodextrin, hydroxypropyl-beta-cyclodextrin, and sulfobutylether beta-cyclodextrin. In certain embodiments, 'Hsieh enhancers' described in U.S. Pat. Nos. 5,023,252 and 5,731,303 or cyclic lactones or cyclic diesters or cyclic ketones described in WO2011153400 A2 can be added as permeation enhancers.

Example lipids for permeation enhancement include, but is not limited to, 1,2-Dioleoyl-sn-Glycero-3 Ethylphosphocholine, 1,2-di-O-phytanyl-glycero-3-phosphocholine, 1-O-hexadecyl-2-acetoyl-sn-glycerol, 1-O-octadecyl-2-O-methyl-glycerol-3-phosphocholine, 16:0-09:0(ALDO)PC, 16:0-09:0(COOH)PC, 3-beta-hydroxy-5alpha-cholest-8 (14)-en-15-one, C10 sucrose, C12 maltose, C12 sucrose, C14 maltose, C16-09:0, C6 glucose, C6 maltose, C7 glucose, C8 glucose, Cardiolipin (sodium salt), Ceramide (brain porcine), Ceramide C10:0, Ceramide C12:0, Ceramide C14:0, Ceramide C16:0, Ceramide C17:0, Ceramide C18:0, Ceramide C18:1, Ceramide C20:0, Ceramide C24:0, Ceramide C24:1, Ceramide C2:0, Ceramide C4:0, Ceramide C6:0, Ceramide C8:0, Cerebroside (brain porcine), Cerebroside Sulfatide (porcine), Dimethylsphingosine, Egg Ceramide, Galactosyl sphingosine, Glucosyl-sphingosine, Lactosyl(B) Sphingosine, Lyso-PAF, N-acetoyl ceramide-1-phosphate, N-octanoyl ceramide-1-phosphate, PGPC1, POVPC, Phosphatidylinositol (Soy), Phosphatidylinositol (bovine), Platelet-Activation Factor, Porcine brain ganglioside, Sphingomyelin (brain porcine), Sphingosine-1-phosphate, and trimethylsphingosine. Preferred lipids in this context are those classified as glycosylated sphingosines, alkylglucosides, oxidized lipids, and ether lipids (PAF).

We have found that a variety of commonly used and generally accepted as safe (GRAS) pharmaceutical excipients act synergistically to increase epinephrine permeation across the nasal mucosa. Said excipients can be demonstrated by their ability to improve epinephrine permeation in vitro, for example in a in vitro tissue model to human mucosa, and also in vivo, for example, animal pharmacokinetic studies. Alternatively, we have also found that near-GRAS and non-GRAS excipients can act synergistically upon the nasal mucosa to increase transmucosal permeation of epinephrine.

It will also be appreciated that permeation enhancers suitable for use in the formulation of drug preparations that enter the bloodstream via the GI tract also potentially may be adapted for use in the present invention. These, without limitation, include those disclosed in US 20030232078, such as ethylene-diamine tetra-acetic acid (EDTA), bile salt permeation enhancers such as those noted above and fatty acid permeation enhancers, such as sodium caprate, sodium laurate, sodium caprylate, capric acid, lauric acid, and caprylic acid, acyl carnitines, such as palmitoyl carnitine, stearoyl carnitine, myristoyl carnitine, and lauroyl carnitine, and salicylates, such as sodium salicylate, 5-methoxy salicylate, and methyl salicylate. U.S. Pat. Nos. 4,548,922 and 4,746,508 also discloses a system for delivering proteins and polypeptides by intranasal or other transmucosal routes using low toxicity permeation enhancers of the amphiphilic steroid family, e.g. fusidic acid derivatives, to promote efficient transport of the drug across the mucosal surface.

For permeation enhancement of epinephrine, the actual effectiveness of an enhancer shall be verified by routine experiments of a nature well known to the skilled artisan, e.g., using the porcine, dog, or rat model. The amount of permeation enhancer included in the epinephrine formulation of the present invention, will generally range between about 1 wt % to about 30 wt %. The precise nature and amount of enhancer will vary depending on, for example, the particular permeation enhancer or enhancer composition selected, and on the nature of other components in the formulation, such as its potency. The upper limit for enhancer concentration is set by toxic effect to or irritation limits of the mucosal membrane or its solubility limits.

(c) Mucosal absorption or transport enhancers, mucosal transit slowing agents and mucoadhesives—Because mucosal membranes provide a protective barrier against the outside environment and are lined by epithelial cells which provide a barrier to the entry of toxins, bacteria and viruses, agents that aid or promote absorption and/or transport of therapeutic agents by getting past the protective barrier are often used in pharmaceutical compositions. Absorption agents used to date include surfactants, gelling microspheres and the bioadhesive polymer, chitosan. Examples of these systems have been reviewed by Ilium L. and Fisher A. M. in "Inhalation Delivery of Therapeutic Peptides and Proteins," Adjei and Gupta (eds.) Marcel Dekker Inc., New York (1997), 135-184 and by Constantino H. R. et al. Intranasal delivery: Physicochemical and Therapeutic Aspects, Int J Pharm, 337, 2007, 1-24. The present invention contemplates adding one or more or combination of the afore-mentioned absorption agents or others including sodium lauryl sulfate, sodium salicylate, oleic acid, lecithin, dehydrated alcohol, Tween, Span, polyoxyl 40 stearate, polyoxyl ethylene 40 stearate, propylene glycol, hydroxyl fatty acid ester of polyethylene glycol, glycerol monooleate, fusieates, bile salts, octoxynol, polysorbate 20, polysorbate 80, DDPC, DPPC, a chelator such as EDTA, EGTA, or citrate, and combinations thereof; or one selected from the group consisting of anionic, cationic and nonionic surfactants. The term enhancer as used in the invention also encompasses substances that are capable of modulating the barrier function of a cellular tight junction.

Since the typical residence time of proteins and other macromolecular species delivered is limited at the nasal mucosa due to rapid mucociliary clearance, e.g., to about 15-30 minutes or less, in some embodiments, substances, compounds or peptides that reduce nasal mucosal transit time can be included in the intranasal epinephrine composition of the present invention. For instance, polyacrylate mucoadhesive agents are known to slow the rate of gastric transit thereby maximizing efficiency of both the protective effect and the time required for delivery of repair agents into the underlying tissue. The present intranasal epinephrine formulation contemplates adding such polyacrylate mucoadhesive agents as disclosed in WO2003037355A1 or similar agents or substances (synthetic or natural) or peptides alone or in combination, that is compatible with epinephrine administration and can slow the rate of nasal transit and maximize the absorption of epinephrine in the nasal mucosa.

Alternatively, the intranasal epinephrine composition of the present invention can include modulatory agents of epithelial junction physiology, such as nitric oxide (NO) stimulators, chitosan and chitosan derivatives.

To promote adhesion of the active ingredients of the pharmaceutical composition, present invention also contemplates adding mucoadhesive agents to the intranasal composition. As used herein, mucoadhesion is a property whereby a natural or synthetic substance, when applied to a mucosal epithelium adheres to or penetrates a subjects's mucosal membrane, in this invention nasal mucosal membranes, for a period of time sufficient to quantitatively deliver an anti-anaphylactic composition provided herein to the subject.

Generally, although not exclusively, adhesion of mucoadhesives to a mucous membrane occurs via secondary chemical bonds, such as hydrogen bonding and Van der Waal forces (Tabor D. 1977, J. Colloid Interface Sci. 58:2 and Good R. J. 1977, J. Colloid Interface Sci. 59:398). Non-limiting examples of one or more or combination of mucoadhesive agents that can be added to the present epinephrine composition include crystalline cellulose, cellulose derivatives, starch, proteins such as mucin, lactoferrin and transferrins, mucoadhesive polymers such as chitosan or carbopol, polyacrylic acid or derivatives such as carbophil, carbomer, and carbopol 943 or lecithin (Takeuchi H. et al. 2005, Adv Drug Deliv Rev, 57:1583-1594).

(d) Pharmaceutically acceptable excipients selected from the group comprising of block copolymers comprising repeating ethylene oxide moieties, anionic polysaccharides and ion exchange polymeric materials, including excipients selected from the group consisting of pectin, carboxylated starch and gellan.

(e) Viscosity enhancing or thickening agents, especially in nasal dry powder delivery, that can also have other desirable actions on the nasal mucosa for increasing API transport or absorption, dissolution rate, or residency time (by mechanisms that are not known), selected from the group comprising of poly (vinyl alcohol) (PVA), poly (ethylene glycol) (PEG), propylene glycol, and polysaccharides such as soluble starch, various cellulose forms both crystalline and amorphous, methylcellulose, hydroxylpropyl cellulose carboxymethylcellulose, and chitosan.

(f) Because epinephrine has been reported to have an unpleasant taste when inhaled (Simons F. E. R. et al. 2000 Pediatrics 106(5): 1040-44), addition of taste-masking agents to the composition is contemplated. The present invention could use a variety of taste-masking agents, including cyclodextran cages to taste-mask. Other agents for taste masking include, but are not limited to citric acid (up to 20% in a marketed nasal solution), sorbitol (up to 2.86% in a marketed metered nasal spray), glycerin (up to 2.5% in a marketed nasal solution), dextrose (5% in a marketed metered nasal spray), and phenethyl alcohol (up to 0.25% in a marketed metered nasal spray, also could serve as a preservative for multi-use). The following agents approved in buccal/oral/dental compositions may also be added in the current formulation: acacia syrup, anethole, anise oil, benzaldehyde, butterscotch, cardamom, cherry (and varieties thereof), cinnamon, cocoa, coriander, ethyl acetate, ethyl vanillin, ginger, glucose, lavender, lemon, maltodextrin, mannitol, methyl salicylate, nutmeg, orange, peppermint, raspberry, saccharin, spearmint, sucrose, sucralose, tolu, vanilla and varieties thereof.

(g) Since sulfites are currently used in all commercially available epinephrine preparations, and can be anaphylactic in susceptible individuals and in individuals with mutations to the sulfatase gene, the present formulation of epinephrine is sulfite-free. Thus sulfite-free, non-toxic preservatives for epinephrine (or other oxidizable drugs) that are non-allergenic and non bronchospasmodic are selected from the group comprising of thiols, glutathione, glutathione reductase, glutathione peroxidase, hydroquinone, amikasin sulfate, apomorphine hydrochloride, metaraminol, levobunonol, levobunonol hydrochloride, acamprosate calcium, fenoldopam, hydrocortisone/neomycin sulfate/polymyxin B, dexamethasone sodium phosphate, hydromorphone, dobutamine, epinephrine, etidicaine/epinephrine bitartrate, gentamycin, tinzaparin, isoproternerol, ketoconazole, sodium sulfacetamide, norepinephrine, bupivacaine/epinephrine bitartrate, morphine, tobramycin, rotigotine, orphenadrine, procaine, nalbuphine, oxytetracycline, nortriptyline, perphenazine, promethazine hydrochloride, prednisolone acetate, propofol, mesalamine, trimethoprim/sulfamethoxazole, carisoprodol/aspirin/codeine, streptomycin, mafenide acetate, tetracycline hydrochloride, pentazocine lactate, chlorpromazine, triethylperazine maleate, fluorinolone acetonide/hydroquinone/tretinoin, acetaminophen/codeine, doxycline calcium and lidocaine/epinephrine.

(h) Stabilizers/preservatives- commercially available epinephrines today all contain stabilizers that are themselves bronchodilators or allergenic at least in sensitive patients, especially asthmatics. These include sodium metabisulfite (0.5 g in EpiPen); and chlorobutanol and sodium metabisulfite (TwinJect™ injection, at unspecified concentrations); or 34% dehydrated alcohol with Vitamin C in Primatene Mist Inhalation Aerosol. The bisulfites, chlorobutanol and alcohol inactive ingredients have all been extensively documented as being contraindicated for bronchospasm, and by implication for anaphylaxis or cardiac arrest. The present invention will be the only formulation of epinephrine on the US market without these bronchospasmodic preservatives, but with only Vitamin C as a possible stabilizer and being sealed in a darkened vial under inert nitrogen. Vitamin C is known to be harmless in relation to lung function, bronchospasm and asthma. Vitamin C is recognized as the major antioxidant in airway surface liquid of the lung, where it is likely protective against toxic oxidants and likely has this effect on the nasal mucosa.

(i) Anti-histamines that not only act to inhibit COMT but also prevents explosive mast cell degranulation activity in response to allergens. The anti-histamines contemplated in the invention include those suitable for nasal application as disclosed in US 20100055152 A1, non-sedating antihistamines disclosed in issued U.S. Pat. No. 8,263,581 and those well known in the art and selected from the group comprising azelastine, hydroxyzine, desloratadine, emadastine, levocabastine, carbinoxamine, levocetrizine, fexofenadine, diphenhydramine, brompheniramine, clemastine, and chlorpheniramine.

(j) Humectants selected from the group comprising of sorbitol, glycerol, mineral oil, vegetable oil, or combinations thereof.

(k) Osmotic adjusting agents, which may be used, include, but are not limited to, sodium chloride, potassium chloride, zinc chloride, calcium chloride, and mixtures thereof. Other osmotic adjusting agents may also include, but are not limited to, mannitol, glycerol, and dextrose and mixtures thereof. In an alternative embodiment, the present invention may comprise about 0.4 to about 1.0 weight percent ionic salt. Preferably, the present invention comprises about 0.9 weight percent of an osmotic adjusting agent.

'Loading dose' in the present invention refers to the actual amount of epinephrine administered intranasally and the 'bioequivalent dose of intramuscularly (IM) or subcutaneously (SQ) injected epinephrine' refers to the blood levels and systemic exposure of intranasal epinephrine attained which is the same or equivalent to intramuscular injection at doses of 0.15 and 0.3 mg in children and adults respectively. 'Effective dose' according to the present invention refers to the epinephrine dose required to treat anaphylaxis or reduce anaphylactic reactions or symptoms or complications in a subject.

API (Active Pharmaceutical Ingredients) or "active ingredients" according to this invention include epinephrine, reversible COMT inhibitor, phentolamine and one or more enabling or additional agents of the present composition.

'Baseline levels' in the present invention refers to epinephrine concentrations in blood before epinephrine administration by intranasal or intramuscular or subcutaneous methods.

The subject is generally a mammal. If a mammal, the subject may be a human, but may also be a domestic livestock, laboratory subject or pet animal.

Modes for Carrying Out the Invention

The intranasal epinephrine compositions of the present invention can be in powder or aqueous formulation.

(a) Powder Formulation

In a preferred embodiment, the composition of the present invention is a dry powder formulation, including one selected from the group consisting of simple powder, crystalline or amorphous mixtures, powder microspheres, coated powder microspheres, including micronized and nanoformulated powders, and combinations thereof. In a related aspect, particles of epinephrine, entacapone and/or phentolamine and enabling agents such as mucoadhesives, mucosal penetration or permeation, absorption or transport enhancers, mucosal transit slowing agents and pharmaceutically suitable carrier such as lactose contained in the powder formulation, can be substantially amorphous or crystalline or semi-crystalline or semi-amorphous or dispersed in nature.

For easy dispensability of the powder formulation the intranasal epinephrine composition of the present invention may further contain additional agents including lubricants such as magnesium stearate, or fluidizing agents such as talc and silicon dioxide. Such lubricants and fluidizing agents are thought to reduce the friction and adhesion among powder particles by adhering onto the powder surface and increasing the space among the particles and, as a result, produce the dispensability improving effect. The powder composition in some embodiments is colorless. In other embodiments, a non-allergenic colorant may be added to the composition to aid in the visualization of the dose to be dispensed from the delivery device.

In some embodiments, the shape and size of the powder particles are either uniform or diverse and are designed to have no negative influence on their absorption in the nasal mucosa. In some other embodiments, the median particle diameter can be up 100 μm, preferably between 50 μm and 100 μm or between 20 μm and 50 μm. Herein the "median diameter" refers to particles of smaller diameters and those with greater diameters. In embodiments where the formulation exists as nanoparticles, less than 10% of particles are less than 10 microns in diameter.

The amount of epinephrine present in the dry powder formulation is between 0.05 mg and 10 mg, preferably from 0.05 mg to 0.75 mg or 0.75 mg to 1.5 mg or 1.5 mg to 3.0 mg or 3.0 to 4.5 mg or 4.5 to 6.0 mg or 6.0 to 7.5 mg or 7.5 to 9.0 mg or 9.0 to 10.0 mg. In some other related embodiments, epinephrine represented in the dry powder formulation is between 0.25% and 50%. Enabling agents including a reversible COMT inhibitor and/or vasodilator present in the formulation ranges between 0.001 mg (or 1 μg) and 10 mg. The total amount of dry powder formulation can be up to 100 mg, but preferably 50, 30, 20, 10 and 5 mg.

In some embodiments, conventional methods are employed to make a suitable powder formulation. This includes mixing powdery drugs with carriers and enabling agents for nasal administration by using mortar, mixers, or stirrer. Other methods to make a suitable powder formulation include, preparation of a solution of active ingredients and excipients, followed by precipitation, filtration, and pulverization, or followed by removal of the solvent by freeze-drying, followed by pulverization or nanosizing of the powder to the desired particle size. The final step can be sieving to obtain particles with a size of less than 100 μm in diameter, preferably between 50 μm and 100 μm or between 20 μm and 50 μm in diameter. In some embodiments, nasal powder compositions made by mixing epinephrine, enabling agents, including mucosal permeation and penetration enhancers, agents that increase nasal residency time, and acceptable excipients, can each possess the desired particle size. One or more pharmaceutical dose of the dry powder composition of the present invention can be administered using a simple hand or finger operated spray device, nasal insufflator, a jet-spray, or any other conventional device known to skilled artisan in the art.

The powder compositions, in preferred embodiments, may be presented in a sterile unit dosage form (for example, in capsules, cartridges, or blister packs) from which the powder may be administered with the aid of a dry powder dispenser or by numerous other nasal delivery methods well known to those skilled in the art.

In certain other embodiments epinephrine is nanoformulated and may be dosed as a reconstituted powder prior to administration, or as a liquid suspension. Nanoformulation of the drug in the present invention utilizes readily available and simple fluid bed spray drying method in a manner that produces uniform and stable 40-90 nm drug particles of pure API without external excipients. This is important since some methods of manufacturing nanopharmaceuticals require the addition of external nanostructures to the API, which raises potential safety concerns. The FDA treats nanoformulated or micronized API the same as a raw drug, with no additional safety concerns.

One of the key advantages of nanoformulation is the tiny size of the API particles and the vast increase in surface area compared to non-nanoformulated API. Other advantages of nanoformulation include (i) higher water solubility of drugs that are poorly soluble in water, due to the increased surface area having a greater exposure to the solubilizing effects of an aqueous media (ii) drug solubility limits may be reduced (iii) absence of any food effects, which can limit patient compliance if a drug must be taken with food or without food (iv) reduced hepatic first pass metabolism by unclear mechanisms and possibly (v) increased rate of membrane transportation because rate-limiting solubility is diminished.

Moreover, a combination of nanoformulation and nasal delivery of epinephrine and enabling drugs (vasodilators and reversible COMT inhibitors, permeation and penetration agents, and residency time modifiers etc.) has surprising synergistic effects on Tmax. The formulation or the nanoformulation of the present invention, when delivered nasally is as fast- acting as intramuscularly injected epinephrine, achieving a Tmax in about 3-8 minutes. This is in contrast to an epinephrine-only formulation which when given as intranasal spray in human subjects reached an unacceptable Tmax in about 70±17 minutes (Nakponetong K. et al. 2010, J Allergy Clin Immunol 125(2): Abstract 859).

(b) Aqueous Formulation

Another aspect of the invention is a composition wherein epinephrine, entacapone and/or phentolamine and the enabling agents are dispersed in aqueous or non-aqueous formulations. In a related aspect, the aqueous solution is selected from the group consisting of aqueous gels, aqueous suspensions, aqueous liposomal dispersions, aqueous emulsions, aqueous microemulsions, aqueous micronized particles, aqueous nanoparticles and combinations thereof. Another aspect is wherein the composition is a non-aqueous solution, including one selected from the group consisting of non-aqueous gels, non-aqueous suspensions, non-aqueous liposomal dispersions, non-aqueous emulsions, non-aqueous microemulsions, non-aqueous micronized particles, and non-aqueous nanoparticles and combinations thereof.

In one embodiment, nanoformulated epinephrine, entacapone and/or phentolamine and enabling agents, including permeation enhancing, absorption and transport enhancing and residency time agents, present in aqueous milieu is used for avoiding first pass metabolism, gaining faster dissolution rate by increasing the solubility of the active pharmaceutical ingredient, and passing the nasal mucosa at a faster rate. This is especially important when the dose must be delivered in only 100-250 µl and such small volume may approach the solubility limits of the active ingredients.

In related embodiments, the pH of the intranasal aqueous formulation can be acidic, for example in the range of pH 3 to pH 6. In a related aspect the pharmaceutical composition comprising an aqueous buffer has a pH from about 3 to 7.5 containing a sufficient amount of a therapeutically acceptable thickening agent so that the viscosity is from about 2500 to about 10,000 cps.

For the administration of powder or aqueous compositions to mucosal membranes, in particular the nasal mucosal membranes, the compositions according to the invention are conveniently delivered by conventional means e.g. in the form of a single dose or multiple dose manual pump nasal spray. The compositions may also be delivered to the lungs by direct inhalation by numerous delivery methods well known to those skilled in the art, particularly for the treatment of mild bronchospasm, such as asthmatics in nighttime bronchoconstriction. For instance, the nasal spray compositions when formulated as pH neutral and isotonic solutions or suspensions may be delivered by a nebulizer. Another embodiment of the invention is a method of nasal delivery that employs a sterile premixed formulation containing epinephrine that may be disposed of after use.

In some embodiments the composition is formulated for delivery as aerosol spray especially when the active ingredients are suspended, optionally together with one or more stabilizers. The aerosol spray device uses a non-halogenated hydrocarbon propellant, including air, nitrogen, or other gases, or manual pump action to deliver the aerosol spray. In a related aspect, the pharmaceutical aerosol device comprises the pharmaceutical composition; a container into which the composition is placed, and an actuator to produce particles of an aerosol spray out of a tip of the actuator when actuated, wherein the aerosol spray consists of droplets, wherein less than 10% of droplets are less than 10 microns in diameter. Another aspect is the device, wherein the aerosol has a spray pattern ellipticity ratio of 1 to 4 when measured at a height of 0.5 cm to 10 cm distance from the actuator tip. Another aspect is the device, wherein the aerosol spray contains 50 to 500 microliters of the solution per actuation, wherein the aerosol spray pattern has major and minor axes of 10 to 50 mm when measured at a height of 0.5 cm to 10 cm distance from the actuator tip, or wherein upon actuation an aerosol of the solution is produced through the tip of the actuator, wherein the aerosol is comprised of droplets of the solution that are 10 to 500 microns in size.

In some embodiments, controlled release of epinephrine may have advantages. Sustained or Controlled Release (CR) can be achieved by a variety of approaches including manipulation of epinephrine to control its dissolution rate, and/or the composition of the medium in which epinephrine is suspended. To achieve the sustained or CR, excipients with mucoadhesive, and/or viscosity enhancing and/or ability to reversibly diminish mucocilliary clearance function can be incorporated into the medium in which the epinephrine is suspended. The approach for achieving the sustained or controlled release may be achieved with epinephrine and/or co-administered vasodilation agents.

In addition to enabling agents in both aqueous and powder intranasal formulations of the present invention, the composition may further contain preservatives, stabilizers, antioxidants, thickening agent, humectant, surfactants, mucoadhesive agents, colorants, one or more excipients or combinations thereof.

To achieve suitable shelf-life, epinephrine has conventionally been combined with preservatives or stabilizers that themselves may be allergenic or even anaphylactic in some susceptible patients. Hence, in one embodiment, the composition of the present invention will be the only formulation of epinephrine without these bronchospasmodic stabilizers and instead contain only Vitamin C as a stabilizer and sealed under inert nitrogen. The novel use of a naturally—occurring enzymatic stabilizing antioxidant system that is part of the human body solves a problem that has plagued the use of epinephrine, and a long list of other drugs that degrade in the presence of oxygen.

In some other embodiments, the present invention may utilize naturally occurring thiols that do not have an unacceptable taste and smell. In yet other embodiments, the present invention utilizes glutathione reductase as a naturally occurring recycling antioxidant to stop the oxidation of epinephrine in solution. It has the advantages of reactive sulfhydryl groups without the noxious smells or flavor of purified thiols, and unlike the purified thiols is enzymatic and self-generating.

In further embodiments, the pharmaceutical composition of the present invention is an isotonic non-irritating formulation for nasal administration, and utilizes the enzymatic antioxidants ascorbic acid (natural vitamin C), glutathione, glutathione reductase and glutathione peroxidase, under sterile nitrogen seal in solution in darkened vials, at concentrations known by those in the art. A similar antioxidant cycling system could also be set up with naturally occurring superoxide dismutase (CuZn—SOD) or superoxide reductase, with catalase or with naturally occurring sulfur containing antioxidant enzymes including: (1) carnosine, a natural muscle enzyme used as a meat preserver; (2) ergothionene from fungi (but not mammals); (3) ovothiol from marine animals and protozoa; (4) lipoic or thioctic acid (used to treat *Amantita* mushroom poisoning); and (5) thioredoxin peroxidase. Recombinant thermostable variants of these various enzymes would confer convenience and shelf life on the enzymes themselves, and can be used in this invention.

In one embodiment, the pharmaceutical composition of present invention is a sterile single or dual-event premeasured, pre-mixed, sterile preparation. In a related embodiment, a process for making a sterile nasal solution without preservatives, of the present invention comprises one or more of the following steps: (1) adding at least a therapeutically effective pediatric or, alternatively adult, amount of epinephrine and enabling drugs and other agents in a vehicle, such as water; (2) placing the mixture in a container, and sterilizing the mixture by steam sterilization, or by any other sterilization means known in the art. Each mixture being filled into a vial, and then packaged under nitrogen gas, sealed, stored and/or used directly. Here, the resulting mixture is stable, and after sterilization, it can be dispersed, if necessary, into multiple mixtures each containing a unit dose of a therapeutically effective amount of epinephrine and enabling drugs suitable for adults or children.

In another embodiment, a process for making a non-sterile nasal solution with preservatives of the present invention comprises one or more of the following steps: (1) adding at least a therapeutically effective pediatric or, alternatively adult, amount of epinephrine in a vehicle, such as water; (2) adding stabilizers such as BAC, and either sodium metabisulfite or ascorbic acids, in sufficient concentrations to achieve a 12-24 month shelf life or more, as is known in the art. Each mixture being filled into a vial, and then packaged under nitrogen gas, sealed, stored and/or used directly. Here, the resulting mixture is stable, and can be dispersed, if necessary, into multiple mixtures each containing a unit dose of a therapeutically effective amount epinephrine suitable for adults or children.

In some embodiments, osmotic adjusting agents may be used in the present composition and include, but are not limited to, sodium chloride, potassium chloride, zinc chloride, calcium chloride, and mixtures thereof. Other osmotic adjusting agents may also include, but are not limited to, mannitol, glycerol, and dextrose and mixtures thereof. In an alternative embodiment, the present invention may comprise about 0.4 to about 1.0 weight percent ionic salt. Preferably, the present invention comprises about 0.9 weight percent of an osmotic adjusting agent.

In some embodiments, the intranasal epinephrine formulations of the present invention could use a variety of taste-masking agents, including cyclodextran cages to taste-mask the unpleasant taste of epinephrine (Simons F.E.R. et al. 2000, Pediatrics 106(5): 1040-44).

Pharmaceutical Product and Doses

In one preferred aspect, the present invention provides a pharmaceutical product, comprising apparatus for intranasally administering a pharmaceutical dose or dose form in accordance with the third aspect of the invention, and a pharmaceutical composition in accordance with the first or second aspect of the invention. The apparatus can comprise a reservoir and means for expelling the pharmaceutical dose in the form of a dry powder or aqueous spray, wherein a quantity of the pharmaceutical composition is contained within the reservoir. In an embodiment, the apparatus comprises a pump spray device in which the means for expelling a dose comprises a metering pump or precise expulsion of the correct dose in a single use device. In an alternative embodiment, the apparatus comprises a pressurized spray device, in which the means for expelling a dose comprises a metering valve and the pharmaceutical composition further comprises a conventional propellant. In some embodiments, the device used to deliver the present composition can be programmed or is programmable before use to deliver a pharmaceutical dose(s). The device may further have audio or visual features to either instruct the user to deliver a pharmaceutical dose and/or indicate the user after the dose is dispensed. Suitable pressurized spray devices are well known in the art and include those disclosed in, WO199211190, WO199709034, U.S. Pat. Nos. 4,819,834, 4,407,481 especially when adapted for producing a nasal spray as opposed to an aerosol for inhalation, or a sublingual spray. Suitable nasal pump spray devices include for instance, the VP50, VP70 and VP100 models available from Valois S. A. in Marly Le Roi, France and the 50, 70 and 100 µl nasal pump sprays available from Pfeiffer GmbH in Radolfzell, Germany, although other models and sizes can be employed. In the aforementioned embodiments, a pharmaceutical dose or dose unit in accordance with the invention can be present within the metering chamber of the metering pump or valve.

As shown in Table 1, the currently available doses offered by EpiPen™ result in physicians being forced to decide whether to underdose (i.e., 1.3-1.7X) or to overdose (i.e., 1.5-3.0 X) a patient based on weight, especially in children. The current invention also provides two nasal sprays: a higher dose for adults, and a lower dose for children. However, unlike Epipen™ that is marketed only in 2 fixed doses (0.15 mg for pediatric use and 0.3 mg for adult use), the concentration of epinephrine (the loading dose) administered in the present invention importantly allows the patient or healthcare professional to choose the number of sprays to administer to achieve the correct or optimal dose for their particular body weight (Table 1). This can be achieved either by having several sprays from a multi-dose pump device or using several single use pumps. Thus the formulation of the present invention has 2 key advantages (i) permits attaining bioequivalent doses of intramuscularly administered epinephrine for both children and adults (ii) permits optimal doses depending on the body weight of the subject in contrast to under- or over dosed subjects using Epipen™.

TABLE 1

Illustrative Optimal Nasal Dosing at all Pediatric Weights

| | Body wt. Kg | | | | | |
|---|---|---|---|---|---|---|
| | ≤5 | 10 | 15 | 20 | 25 | ≥30 |
| Optimal epinephrine Dose (mg) | 0.05 | 0.1 | 0.15 | 0.2 | 0.25 | 0.3 |
| EpiPen Jr dose (mg) | 0.15 | 0.15 | 0.15 | 0.15 | 0.15 | 0.15 |
| Overdose: | 3× | 1.5× | Optimal | | | |
| Underdose: | | | | 1.3× | 1.7× | 2.0× |
| Nasal Epinephrine* | | | | | | |
| Sprays total | 1 | 2 | 3 | 4 | 5 | 6 |
| Sprays per nostril | 1 | 1 | 1.5 | 2 | 2.5 | 3 |
| Dose (mg) | 0.05 | 0.1 | 0.15 | 0.2 | 0.25 | 0.3 |
| Optimal dosing | ←---------------- Optimal ----------------→ | | | | | |

*Note that the nasal loading dose will be adjusted to give blood bioequivalent doses for IM administration.

For instance, as shown in Table 1, assuming that the loading dose in the present formulation (in a Nasal Epinephrine Jr. nasal product) is bioequivalent to the IM systemic blood epinephrine levels (pediatric dose of Epipen™ is 0.15 mg/0.3 mL or 0.05 mg/100 a single spray could be 0.05 mg dose per 100 µL and up to 3 sprays would deliver the blood equivalent of an IM injection of 1.5 mg and 6 sprays (i.e.: 3 sprays per nostril) would deliver the blood equivalent of an intramuscular injection of 0.3 mg in a pediatric patient weighing about 30 Kg. In the adult Nasal Epinephrine product, the initial dose would be bioequivalent of 0.3 mg intramuscular dosing, and if more was needed an additional 6 sprays would be available. Naturally, these loading doses may be adjusted for the actual kinetics of nasal delivery in this composition in order to achieve the bioequivalent of the intramuscular dose. After each anaphylactic event, the disposable nasal spray device would be discarded as the nitrogen seal would be broken and the unit would no longer be sterile. This formulation and drug-device combination meets the mg/kg drug dosing flexibility that clinicians have been trying to achieve for many years. Unlike Primatene Mist, which took up to 20 inhalation doses to come close to therapeutic levels (Simons F.E.R. et al. 2000 Pediatrics 106(5): 1040-44), each nasal spray can be manually actuated by either the patient or caregiver, and only 100-250 µL in volume or 100 mg, requiring no inspiratory effort by the patient. The present invention also permits utilizing the customizable ideal dosing (0.01 mg/kg body weight) according to the Tables 2 and 3 below.

TABLE 2

Illustrative Customizable Ideal Dosing for Children

| Drug | Dose per Spray*** | | | | | |
|---|---|---|---|---|---|---|
| 1. PEDIATRIC: | | | | | | |
| Nasal Sprays total* | 1 | 2 | 3 | 4 | 5 | 6 |
| Pediatric Body weight (Kg) | ≤5 | 10 | 15 | 20 | 25 | ≥30 |
| Epinephrine actual dose: 0.05 mg | 0.05 | 0.1 | 0.15 | 0.2 | 0.25 | 0.3 |
| Optimal Dose: | 0.05 | 0.1 | 0.15 | 0.2 | 0.25 | 0.3 |
| Phentolamine actual dose: 0.5 mg | 0.1 | 1.0 | 1.5 | 2.0 | 2.5 | 3.0 |
| Optimal Dose: 0.6-30 mg/mL spray | | | | | | |
| Entacapone actual dose: 0.1 mg | 0.1 | 0.2 | 0.3 | 0.4 | 0.5 | 0.6 |
| Optimal dose under 20 mg/spray | | | | | | |

TABLE 3

Illustrative Customizable Ideal Dosing for Adults
2. ADULT**: Dosage is one spray, unless treatment a failure or rebound anaphylaxis requires a second, to a maximum of four additional doses total for refractory patient or rebound anaphylaxis; note that the loading doses are illustrative and would be adjusted for bioequivalence to IM injection of epinephrine

| | Sprays total* | | | |
|---|---|---|---|---|
| | 1 | 2 | 3 | 4 |
| Adult Body weight (Kg) | ≥30 | ≥60 | ≥90 | ≥120 |
| Epinephrine actual dose: | 0.3 mg | 0.6 | 0.9 | 1.2 |
| Optimal Dose: | 0.3 mg | na | na | na |
| Phentolamine actual dose: | 0.5 mg | 0.5 | 1.0 | 1.5 |
| Optimal Dose: | 0.1-30 mg/mL spray | | | |
| Entacapone actual dose: | 0.1 mg | 0.1 | 0.2 | 0.3 |
| Optimal dose: | 0.1-20 mg/spray | | | |

*Sprays divided between two nostrils; so for total 6 sprays, it is 3 sprays per nostril; for total 3 sprays, it is 2 sprays in one nostril, 1 spray in the other, and so forth. For Adult dosing, there would be four total sprays of 0.3 g each spray available, if the first spray were ineffective.
*** Spray volume is targeted at 100 µL each spray.

This gives target concentrations of:

| | Dose per Spray | | Concentration* | |
|---|---|---|---|---|
| | Pediatric | Adult | Pediatric | Adult |
| Epinephrine | 0.05 g | 0.30 g | 0.5 mg/mL | 1.0 mg/mL |
| Phentolamine | 0.5 mg | 0.5 mg | 50 mg/mL | 50 mg/mL |
| Entacapone | 0.1 mg | 0.1 mg | 10 mg/mL | 10 mg/mL |

*Assume 100 µL per dose spray

Therefore unlike the marketed intramuscular epinephrine injections that are available in only two fixed doses of epinephrine, the nasal spray dosage can be adjusted 10-fold in pediatric use and 10-fold in adult use, by administering only up to three sprays into each nostril, suitable for giving an exact ideal-body-weight-adjusted dose of each drug, without the need for mixing. This means that the patient can receive the exact weight-matched optimal doses, or if non-responsive, additional doses. Additionally, the present formulation can be delivered as a second dose from the same device in the case of rebound anaphylaxis. Finally, by intranasal administration of present formulation the current invention obviates the documented problem that the increasing obesity epidemic has caused the length of the EpiPen™ autoinjector needle to be insufficient to achieve intramuscular dosing, but rather subcutaneous dosing with the ineffective Tmax.

Herein, the loading dose (i.e., amount of epinephrine administered nasally) results in a bioequivalent dose (in terms of peripheral blood levels and systemic exposure of epinephrine) of intramuscularly injected epinephrine, which is 0.15 in children and 0.3 mg in adults, respectively. Thus, the blood bioequivalent epinephrine target levels, and the loading doses of vasodilator and COMT inhibitor are a ratio of (epinephrine): (phentolamine): (entacapone) in the compositions according to the invention is preferably within the range of (0.15 mg: 0.5 mg; 0.1 mg) for pediatric dosing to (0.3 mg: 0.5 mg: 0.1 mg) for adult dosing. This may be increased six fold proportionately to give the estimated maximal blood doses (i.e., the blood equivalent of intramuscularly injected EpiPen™), respectively.

Upon intranasal administration of the loading dose in either powder or aqueous form, the increase in epinephrine levels is at least the same or equivalent to intramuscularly injected epinephrine. In another embodiment, the increase in epinephrine levels in the blood is 2-fold more than the baseline (i.e., levels prior to epinephrine administration). In related embodiments, intranasal administration of the present composition elicits between 2-fold and 15-fold increase in the epinephrine levels in blood within 30 minutes of said administration. In some embodiments, the increase in epinephrine levels is observed within 15 minutes, or preferably within 10, 5, 3, 2, and 1 minute and the level is sustained in the blood for at least 90, 60, 30, 20 minutes after administration. In further embodiments, the increased epinephrine concentration in the blood is sustained for 60, 40 and 30 minutes.

Therapeutic Methods of Using the Formulation in the Treatment of Anaphylaxis

The present invention provides methods of reducing an anaphylactic reaction in an individual, methods of reducing a symptom of anaphylaxis, methods of reducing the risk of a full-blown anaphylactic response, bronchospasm, and cardiac arrest in an individual, or for treating a subject in cardiac arrest outside ER or in the battlefield or during hypotensive shock and methods of reducing the incidence of the same. The methods generally comprise administering an effective amount of the compositions of the present invention to the mucosal surfaces of the nasal cavities of an individual. The methods are useful to treat an anaphylactic response. Accordingly, the invention further provides methods of treating anaphylaxis in an individual.

Pharmaceutical compositions, doses or products in accordance with the present invention are useful in the treatment of human conditions known to be responsive to epinephrine, including anaphylaxis, and for rescuing a subject in bronchospasm or cardiac arrest. They also provide a fast onset time and are suitable for intranasal use. Although not wishing to be bound by any particular theory, it is considered that the capacity of compositions in accordance with the present invention for providing high blood plasma epinephrine concentrations very rapidly after administration, on the basis of optimal doses of epinephrine, leads to their enhanced efficacy and reduces the likelihood of any unwanted side effects being caused.

In a yet further aspect of the present invention, there is provided the use of epinephrine in combination with one or more enabling agents, mucosal penetration agents, mucosal transit agents, for the preparation of a pharmaceutical composition, dose or product in accordance with any previously described aspect of the invention, for treating anaphylaxis, or bronchospasm or during CPR. The preferred unit dose is 0.05 mg to 10 mg epinephrine, 0.001 mg to 10 mg of entacapone and/or 0.001 mg to 10 mg phentolamine. For making dose units, any pharmaceutically acceptable additives or excipients that do not interfere with the function of the active ingredients can be used.

The invention is further illustrated by the following examples.

The following compositions are prepared as illustrative aqueous solutions of the named drugs suitable for use as nasal drops of nasal spray. In each case, the pH of the final composition is adjusted with pharmaceutically acceptable acid or base to achieve a pH in the range of pH 3 to 9, for example in the range of pH 4 to pH 8, for example in the range of pH 7 to 8. The final osmolality of the formulation is adjusted with a pharmaceutically acceptable tonicifying agent, for example sodium chloride, to achieve a final in osmolality in the range of 10 to 2000 mOsm/kg, for example in the range of 50 to 1000 mOsm/kg, for example in the range of 100 to 500 mOsm/kg, for example in the range of 270 to 330 mOsm/kg (the latter representing isotonic case).

Example 1

Specific Aqueous Intranasal Formulation Containing Epinephrine, Entacapone and Phentolamine To obtain the desired intranasal composition for the treatment of anaphylaxis or bronchospasm, a specific aqueous intranasal formulation may be formulated using nanoformulated reagents in volumes up to 250 μl, and other vasodilators or reversible COMT inhibitors at appropriate concentrations. An aqueous composition comprised of the following components (per 1 mL volume):
0.5-100 mg epinephrine,
1 mg polysorbate 80,
2 mg methylcellulose,
0.08 mg entacapone,
0.5 mg phentolamine hydrochloride,
sodium chloride q.s. to provide osmolality in the range of 200 to 350 mOsm/kg, and
hydrochloric acid q.s. to adjust pH to 3.5-5.0. The aqueous composition is sterile filled into a vial affixed with a nasal aqueous spray pump for delivery of 0.1 mL of atomized product per discharge at a fill volume sufficient to provide at least 2 doses.

In another embodiment of this example, an aqueous composition comprise of the following components (per 1 mL volume):
0.5 mg epinephrine maleate,
1 mg polysorbate 80,
2 mg methylcellulose,
1 mg dipivefrin hydrochloride as vasodilator,
sorbitol q.s. to provide osmolality in the range of 200 to 350 mOsm/kg, and citric acid q.s. to adjust pH to 5.0 - 7.0. The aqueous composition is sterile filled into a vial affixed with a nasal spray pump for delivery of 0.1 mL of atomized product per discharge at a fill volume sufficient to provide at least 2 doses.

In certain other embodiments of this example, the epinephrine as described in the aqueous formulation above is epinephrine hydrochloride or epinephrine maleate and the amount present in 1 mL of the composition preferably is, 0.5 mg or 1.5 mg or 1.75 mg or 2.5 mg or 2.75 mg or 3.0 mg or 3.5 mg or 4.0 mg or 4.5 mg or 5.0 mg or 10.0 mg or 15.0 mg or 20.0 mg or 25.0 mg or 30.0 mg or 35.0 mg or 40.0 mg or 45.0 mg or 50.0 mg or 55.0 mg or 60.0 mg or 65.0 mg or 70.0 mg or 75.0 mg or 80.0 mg or 85.0 mg or 90.0 mg or 95.0 mg or 100 mg.

The above-described formulations may additionally contain 1 mg DDPC, 1 mg EDTA and 10 mg methyl-beta-cyclodextrin as nasal permeation enhancers.

Example 2

Dry Powder Formulation of Epinephrine

A 20 mg dry powder formulation is prepared from the following ingredients: 0.15 mg or 0.3 mg or 0.75 mg or 1 mg epinephrine powder (from SIGMA-ALDRICH) mixed with one or more enabling agents including 0.0001 mg or 0.1 mg entacapone (a reversible COMT inhibitor) and/or 0.0001 mg or 0.5 mg phentolamine (vasodilator) and 1.5 mg suitable carrier, for instance lactose, and suitable penetration enhancer and mucosal transit agent. The average particle diameter of each of the ingredient is within 30 μm. The sterile formulation can then be packaged into vials or nasal spray devices for delivery into nasal mucosa of test subjects.

Testing of Dry Powder Formulation

The pharmacokinetic study of intranasal dry powder epinephrine formulations will be tested in animal models such as cynomolgus (macaque) monkeys. The animals (approximately, 5-7 in no.) will be handled in compliance with the Animal welfare Act and will be examined and evaluated at regular intervals by study personnel. Enough care will be taken to ensure no test-article related abnormalities are noticed in any macaque. Before the experiment, the animals will be divided into following groups:
control 1 (IM placebo),
control 2 (intranasal spray with carrier only)
test group 1 (IM epinephrine)
test group 2 (intranasal spray of epinephrine and suitable carrier),
test group 3 (intranasal spray of epinephrine, carrier and entacapone) or
test group 4 (intranasal spray of epinephrine, carrier and phentolamine)
and will be anesthetized by injection of suitable anesthetic, for example, tiletamine/zolazepam (6 mg/kg). Animals in test group 1 will receive an IM injection of 0.15 mg and those in test group 2 will receive a 20 mg dry powder nasal spray of a composition containing, either 0.75 mg, 1.5 mg or 3.0 mg of epinephrine. Animals in test group 3 will receive 1.5 mg of epinephrine and 0.001 mg or 0.01 mg or 0.5 mg of entacapone while those in test group 4 will receive 1.5 mg epinephrine and 0.5 mg or 0.75 mg of phentolamine. The carrier present in the composition can be lactose or any other pharmaceutically acceptable excipients or enabling agents disclosed in the present invention. When multiple doses are investigated, the animals will be allowed to recover for at least 7- 10 days between each dosing. Blood samples from each group will be collected pre-dose, 2, 3, 5, 8, 10, 15, 20, 25, 30, 45, 60, 90, 120 and 180 minutes after dosing and the epinephrine concentrations in the blood plasma shall be analyzed.

Example 3

Nano-Formulation of Epinephrine (Powder) for Aqueous Reconstitution Before Use

U.S. Pat. No. 7,078,057 B2 by Kerkhof is referenced herein in its entirety with regards to the nanoformulation method of preference. In this disclosure, fluid bed spray drying is employed to manufacture pure API into uniform and stable 40-80 nm particles. These particles can be provided for direct intranasal formulation.

In another embodiment of this example, the nanoformulated epinephrine particles are blended with larger particles of a suitable pharmaceutically acceptable carrier, for instance lactose. For example, the nanoformulated epinephrine coated lactose particles is in the size range (i.e., Dv, 50) of 10 microns to 500 microns, for example in the range of 30-100 microns, for example about 50 microns. It is desired to minimize the fraction of nanoformulated epinephrine coated lactose with size less than 10 microns, for example no more than 10% of particles with size less than 10 microns, for example no more than 1% of particles with size less than 10 microns.

In another embodiment of this example, the nanoformulated epinephrine also contains a vasodilation agent which can be incorporated into the same nanosized particles containing epinephrine, or can be produced separately as nanoparticles, then subsequently the epinephrine nanoparticles and the vasodilating agent nanoparticles can be blended as a co-mixture; both of these cases can also be envisioned to be further blended with lactose particles in order to provide a particle size suitable for nasal administration.

Example 4

Nanoformulation of Epinephrine (Suspension)

U.S. Pat. No. 7,078,057 B2 by Kerkhof is referenced herein in its entirety with regards to the nanoformulation method of preference. In this disclosure, fluid bed spray drying is employed to manufacture pure API into uniform and stable 40-80 nm particles. These particles can be further formulated as a suspension for intranasal administration at the time of use. Such a nasal reformulation device can have the aqueous and nanoformulated dry powder mix at the time of the plunger activation. The suspension milieu can contain various pharmaceutically acceptable excipients, permeation agents, mucosal transit agents, including solvents, pH agents, stabilizers, tonicifying agents, viscosity enhancing agents, dispersing agents such as surface active agents, nasal absorption enhancers, chelators, and preservatives. Alternatively, the suspension nanoformulation of epinephrine can be preservative free.

Example solvents for the suspension nanoformulation of epinephrine include water, and non-aqueous solvents such as ethanol, and low molecular weight poly (ethylene glycols).

Agents for adjusting pH in suspension nanoformulation of epinephrine include buffer systems. Said buffer systems include, but are not limited to, acetate, citrate, succinate, phosphate, amino acids, and tromethamine. Pharmaceutically acceptable acid or base can be added to achieve a pH in the range of pH 3 to 9, for example in the range of pH 4 to pH 8, for example in the range of pH 7 to 8.

Example stabilizers for the suspension nanoformulation of epinephrine include sugars and other polyols, amino acids, and various antioxidant as described in detail herein.

Example tonicifying agents for the suspension nanoformulation of epinephrine includes pharmaceutically acceptable sugars and other polyols (such as, but not limited to, trehalose, mannitol, and sorbitol) and salts (such as, but not limited to, sodium chloride). The final osmolality of the formulation is adjusted with a pharmaceutically acceptable tonicifying agent, for example sodium chloride, to achieve a final in osmolality in the range of 10 to 2000 mOsm/kg, for example in the range of 50 to 1000 mOsm/kg, for example in the range of 100 to 500 mOsm/kg, for example in the range of 270 to 330 mOsm/kg (the latter representing isotonic case).

Example 5

Blended Aqueous Epinephrine Formulation

U.S. Pat. No. 6,702,997 teaches the production of a pulmonary liquid inhalation nebulized spray for pediatric asthmatic patients. In this example, their target concentrations for the nebulizer solution were 0.63 mg/3 mL or 1.25 mg/3 mL for pediatric dosing. In contrast, the present invention targets a highly concentrated solution of epinephrine, so that the effective dose is not 3 mL but about 100 uL. To achieve this level of solubility of the drug with the COMT inhibitor and vasodilator, mucosal transport agents, mucosal transit agents, as well as the enzymatic antioxidants (hereafter excipients), either (1) as a sterile solution bottled under nitrogen gas in opaque bottles, or (2) as a non-sterile solution with added preservatives bottled under nitrogen in opaque bottles, we have employed strategies to achieve high concentrations of the drugs in aqueous solution. These include the use of PEG, lipid and zwitterionic solubilizers, the use of alternative salts of the active drugs, as well as specific nasal mucosal tight junction permeation agents. Such agents include, but are not limited to, chelators (such as EDTA), surface-active agents (such as DDPC or Tween-20 or Tween-80), tight junction modulating peptides, and cyclodextrins.

Herein is described the process for making a single unit dose, sterile, premixed, premeasured and preservatives-free solution for the fixed dose combination (FDC) for nasal epinephrine and the enabling drugs and excipients for the treatment of anaphylaxis. In such an embodiment, the method of the present invention comprises one or more of the following steps: (1) adding at least a therapeutically effective pediatric or, alternatively adult, amount of epinephrine and excipients in a vehicle, such as water; (2) optionally sterilizing the solution and sealing the container. An osmotic adjusting agent may be added to adjust the isotonicity of the solution. In one embodiment of the present invention, the solution of the present invention is isotonic. Isotonicity may be achieved by adding an osmotic adjusting agent to adjust the isotonicity of the solution from about 280 to about 320 mOsm/kg. In addition, an acid (e.g., sulfuric acid) may be added to adjust the pH of the solution to between 3.0 to about 4.0, preferably at about 3.5.

In an alternative embodiment, the nasal solution of the present invention may be prepared as follows: (1) fitting a high density polyethylene (HDPE) or stainless steel formulation tank with a bottom drain and peristaltic recirculation system (for HDPE) or tri-blender (for stainless steel) for mixing; (2) filling the tank with approximately 90% of the required amount of Purified Water USP at a temperature of between 18.degree. C to 25. degree. C; while mixing; (3) adding sulfuric acid, Sodium Chloride USP, and at least a therapeutically effective amount of pediatric Epinephrine USP and excipients to the tank; (4) continue mixing until all chemical components are dissolved; (5) adding Purified Water USP to adjust the final volume, if necessary, thus producing the epinephrine mixture. From the formulation tank, the epinephrine mixture is pumped out through sanitary delivery lines directly into a form-fill-seal (FFS) machine. The epinephrine mixture passes through a 0.2 micron sterilizing cartridge filter, to the filling nozzles within the sterile air shower compartment, and subsequently into formed vials of glass or low density polyethylene (LDPE) that have been silkscreened to prevent light entering. The epinephrine mixture being sterile filled under nitrogen gas into the vials such that each vial contains a single unit doses per pump action of a therapeutically effective amount of epinephrine suitable for adults and children. The filled vials are then sealed. The machine may form, fill and seal the vials in a continuous operation under aseptic conditions, thus producing a sterile product. For example, cards of five filled vials are overwrapped into a protective laminated foil pouch using an auto wrapper machine. Five to twelve such pouches may then be packaged in a shelf carton, thus forming a prepackaged therapeutic system for relieving anaphylaxis, cardiac arrest and bronchospasm. An appropriate label and instructions may be added in the shelf carton.

In an alternative embodiment of the present invention, the epinephrine solution with or without the added preservatives is still filled under nitrogen gas, but not under sterile conditions.

I claim:

1. A pharmaceutical composition comprising:
   (a) an anti-anaphylactic agent, wherein the anti-anaphylactic agent is epinephrine, and
   (b) a vasodilator, wherein the vasodilator is phentolamine, wherein said composition is an aqueous formulation with a pH in the range of 3 to 9, and the formulation provides a dose of about 0.05 mg to about 10 mg of epinephrine and about 0.001 mg to about 10 mg of phentolamine for a human patient.

2. The pharmaceutical composition according to claim 1, further comprising one or more agents selected from the group consisting of, pharmaceutically acceptable excipients, epinephrine potentiators, mucosal permeation or penetration enhancers, mucosal transit slowing agents, mucosal absorption or transport enhancers, mucoadhesives, non-sulfite stabilizers, preservatives, thickening agents, humectants, antihistamines, solubilizing agents, taste-masking agents, antioxidant enzymes, viscosity enhancing agents, dispersing agents, or any combination thereof.

3. The composition according to claim 1, further comprising a reversible COMT inhibitor, wherein the reversible COMT inhibitor is entacapone, or its pharmaceutically acceptable salt or prodrug thereof.

4. The composition according to claim 3, wherein the amount of entacapone is about 0.008 mg to about 0.2 mg per kg body weight of a the human patient.

5. The composition as in claim 1, wherein the composition is formulated as a nasal spray characterized for a single or multiple use.

6. The composition as in claim 1, wherein the composition is configured to be used in the treatment of a condition selected from the group comprising, anaphylaxis, bronchospasm and cardiac arrest.

7. A pharmaceutical product comprising, a device for intranasal administration dispensing a pharmaceutical composition, wherein the pharmaceutical composition comprising:
   (a) an anti-anaphylactic agent, wherein the anti-anaphylactic agent is epinephrine, and
   (b) a vasodilator, wherein the vasodilator is phentolamine, wherein said composition is an aqueous formulation with a pH in the range of 3 to 9, and the formulation provides a dose of about 0.05 mg to about 10 mg of epinephrine and about 0.001 mg to about 10 mg of phentolamine for a human patient.

8. The pharmaceutical product of claim 7, wherein the device comprises a reservoir and means for expelling the pharmaceutical composition in the form of a spray, wherein a quantity of the pharmaceutical composition is contained within the reservoir.

9. A method of treating anaphylaxis or bronchospasm or cardiac arrest in a subject, wherein the method comprises administering intranasally a pharmaceutical composition comprising:
   (a) an anti-anaphylactic agent, wherein the anti-anaphylactic agent is epinephrine, and
   (b) a vasodilator, wherein the vasodilator is phentolamine, wherein said composition is an aqueous formulation with a pH in the range of 3 to 9, and the formulation provides a dose of about 0.05 mg to about 10 mg of epinephrine and about 0.001 mg to about 10 mg of phentolamine for a human patient.

10. The method of claim 9, wherein the pharmaceutical composition further comprises agents selected from the group comprising pharmaceutically acceptable excipients, epinephrine potentiators, mucosal permeation or penetration enhancers, mucosal transit slowing agents, mucosal absorption and transport enhancers, mucoadhesives, non-sulfite stabilizers, preservatives, thickening agents, humectants, antihistamines, solubilizing agents, taste masking agents, antioxidant enzymes, viscosity enhancing agents, dispersing agents, or any combination thereof.

11. The method of claim 9 further comprises adjusting a dose of the epinephrine according to the weight of the subject at an increment of at least 0.01 mg/kg or repeating the dose of the epinephrine more than once if the subject is refractory or experiences rebound anaphylaxis.

* * * * *